United States Patent
Factor et al.

(10) Patent No.: US 11,660,279 B2
(45) Date of Patent: *May 30, 2023

(54) THERAPEUTIC AGENTS FOR TREATING RESTLESS LEG SYNDROME

(71) Applicant: INTRABIO LTD, London (GB)

(72) Inventors: Mallory Factor, Oxford (GB); Michael Strupp, Marchioninistr (DE)

(73) Assignee: INTRABIO LIMITED, London (GB)

( * ) Notice: Subject to any disclaimer, the term of this patent is extended or adjusted under 35 U.S.C. 154(b) by 200 days.

This patent is subject to a terminal disclaimer.

(21) Appl. No.: 16/968,919

(22) PCT Filed: Feb. 14, 2019

(86) PCT No.: PCT/IB2019/051214
§ 371 (c)(1),
(2) Date: Aug. 11, 2020

(87) PCT Pub. No.: WO2019/159110
PCT Pub. Date: Aug. 22, 2019

(65) Prior Publication Data
US 2021/0046031 A1    Feb. 18, 2021

Related U.S. Application Data

(60) Provisional application No. 62/631,383, filed on Feb. 15, 2018.

(51) Int. Cl.
*A61K 31/198* (2006.01)
*A61P 25/00* (2006.01)

(52) U.S. Cl.
CPC ............ *A61K 31/198* (2013.01); *A61P 25/00* (2018.01)

(58) Field of Classification Search
CPC ............................. A61K 31/198; A61P 25/00
See application file for complete search history.

(56) References Cited

FOREIGN PATENT DOCUMENTS

| RU | 2 458 049 C2 | 8/2012 |
|---|---|---|
| WO | WO 2005/027850 A2 | 3/2005 |
| WO | WO 2007/117431 A2 | 10/2007 |
| WO | WO 2011/151685 A1 | 12/2011 |
| WO | WO 2015/129527 A1 | 9/2015 |
| WO | WO 2018/029658 A1 | 2/2018 |
| WO | WO 2018/229738 A1 | 12/2018 |
| WO | WO 2019/078915 A1 | 4/2019 |

OTHER PUBLICATIONS

Strupp et al., Effects of acetyl-DL-leucine in patients with cerebellar ataxia: a case series, Journal of Neurology, vol. 260, 2556-2561, Jul. 9, 2013 (Year: 2013).*
Pedroso et al., Sleep disorders in cerebellar ataxias, Arq Neuropsiquiatr, vol. 69(2-A), 253-257, 2011 (Year: 2011).*
Bremova, et al., "Acetyl-DL-leucine in Niemann-Pick Type C" A Case Series, 2015 American Academy of Neurology.
Buchfuhrer, "Strategies for the Treatment of Restless Leg Syndrome", Neurotherapeutics (2012) 9:776-790.
Dos Santos, et al., "Treatment of Sleeping Disorders Should Be Considered in Clinical Management of Parkinson's Disease", Frontiers in Aging Neuroscience, Oct. 9, 2014.
Porter, et al., "Sleep, Cognition and Dementia", Curr Psychiatry Rep (2015) 17:97, Springer Science+Business Media New York 2015.
Schniepp, et al., "Acetyl-DL-leucine Improves Gait Variability in Patients with Cerebellar Ataxia—A Case Series" Cerebellum & Ataxias (2016) 3:8.
Velazquez-Perez, et al., "Lisuride Reduces Involuntary Periodic Leg Movements in Spinocerebellar Ataxia Type 2 Patients", Cerebellum (2012) 11:1051-1056.
International Search Report & Written Opinion, PCT/IB2019/051214, dated May 28, 2019.
Search report in counterpart Russian Application No. 2020130199 dated Mar. 3, 2022 (2 pages).
Japanese Office Action dated Nov. 16, 2022, in counterpart Japanese Patent Application No. 2020-543526, (42 pages).

* cited by examiner

*Primary Examiner* — Kortney L. Klinkel
*Assistant Examiner* — Padmaja S Rao
(74) *Attorney, Agent, or Firm* — Finnegan, Henderson, Farabow, Garrett & Dunner, LLP

(57) ABSTRACT

The present disclosure provides for treatments of restless legs syndrome (RLS) or one or more symptoms associated with RLS comprising administering leucine, acetyl-leucine or a pharmaceutically acceptable salt thereof.

18 Claims, No Drawings

THERAPEUTIC AGENTS FOR TREATING RESTLESS LEG SYNDROME

This application is the United States national stage entry under 35 U.S.C. § 371 of International Application No. PCT/IB2019/051214, filed on Feb. 14, 2019, and published as WO 2019/159110 A1, which claims priority to U.S. Provisional Application No. 62/631,383, filed Feb. 15, 2018, both of which are incorporated herein by reference in their entirety.

Restless legs syndrome (RLS), also known as Willis-Ekborn disease, is a neurological disorder reported to affect about 10% of adults with higher prevalence in women and older people. RLS is characterized by an overwhelming urge to move one's body, typically accompanied by uncomfortable or odd sensations. It most commonly affects the legs, particularly between the knee and ankle, but can affect other areas, such as the arms, torso, or even phantom limbs. RLS sensations can range from pain or an aching in the muscles, to "an itch you can't scratch," an unpleasant "tickle that won't stop," or even a "crawling" feeling. The sensations may begin or intensify during quiet wakefulness, such as when relaxing, reading, studying, or trying to sleep. For example, sitting or lying down (e.g., reading, plane ride, watching TV) can trigger the sensations and urge to move.

Diagnostic criteria for RLS may include the presence of 1) an urge to move the limbs with and without sensations; 2) worsening at rest; 3) improvement with activity; and 4) worsening in the evening or night. The symptoms of RLS can make sleeping very difficult, and significant daytime difficulties may also result, such as excessive daytime sleepiness as well as depression and anxiety. A prevalent symptom of RLS (but not exclusive to RLS) is known as periodic leg movements of sleep (PLMS), which occurs most typically in the lower limbs and is associated with sleep disruption. The movements often occur about every 20-40 seconds and typically range from brief muscle twitches, jerking movements, or an upward flexing of the feet. The movements often cluster into episodes lasting anywhere from a few minutes to several hours.

The uncomfortable or unpleasant sensations associated with RLS are often temporarily alleviated by movement, such as by continuous, fast up-and-down movements of the leg, and/or rapidly moving the legs toward then away from each other. The sensations—and the need to move—may return immediately after ceasing movement or at a later time.

RLS may start at any age, including childhood, and is a progressive disease for most individuals. Primary RLS is considered idiopathic or with no known etiology. Primary RLS can be progressive and get worse with age. A family history of RLS is common, suggesting a genetic or hereditary link. RLS in children is often misdiagnosed as growing pains. Secondary RLS is usually associated with an underlying medical condition or the use of certain drugs. Secondary RLS often starts later in life and can be associated with more rapid progression but may resolve when the underlying condition is treated. Studies have hypothesized that the pathophysiology of RLS may be linked to abnormalities in the dopaminergic system and iron metabolism.

RLS severity varies and can be measured using one or more of several scales. A widely reported rating scale known as the International Restless Legs Syndrome Study Group Rating Scale ("IRLS") was developed by the International Restless Legs Syndrome Study Group ("IRLSSG") (Walters et al., Validation of the 15 International Restless Legs Syndrome Study Group rating scale for restless legs syndrome. Sleep medicine. 2003 Apr 01; 4(2)1 21-32). The IRLS is a 10-item scale with scores ranging from 0 (no symptoms) to 40. Scores>30 are considered very severe, severe (Score 21-30), moderate (scores 11-20) and 0, mild. Use of the scale is common for clinical assessment, research and therapeutic trials with RLS.

Mild RLS may result in only minor annoyance; however, severe RLS can have a crippling impact on quality of life. It can interfere with work or social activities and reduce function and emotional well-being. RLS-induced sleep disruption may lead to poor daytime functioning, anxiety, and depression. Additional long-term complications from sleep disruption could include adverse cardiovascular events. Sleep deprivation and daytime fatigue are common reasons RLS patients seek treatment. A primary goal of RLS treatment is to manage symptoms and improve patient function, daytime fatigue and quality of life.

Treatment of RLS is often with levodopa or a dopamine agonist, such as pramipexole or ropinirole. These drugs, however, are typically associated with undesired side effects. One significant treatment complication with long-term use of dopaminergic agents is a drug-induced worsening of symptoms known as augmentation. Augmentation is characterized by more intense symptoms with earlier onset, shorter latency, and that may spread to other body parts (usually the arms, but also the trunk and face). Impulse control disorders have also been reported in a significant percentage of RLS patients using these drugs for long term.

Thus, there is a need for more effective treatment of RLS and its symptoms without the undesirable side effects associated with existing drug therapy.

The present disclosure addresses this need and describes leucine and acetyl-leucine for treating RLS.

Acetyl-leucine in racemate form (acetyl-DL-leucine) and salts of the same have been used in the treatment of vertigo of various origins, notably Meniere's vertigo and vertigo of inflammatory (vestibular neuritis) or toxic origin. For example, acetyl-leucine is marketed by Pierre Fabre Medicament in racemate form as an anti-vertigo medicament under the name Tanganil®. Clinical results of Tanganil® reported by various authors demonstrate an improvement in vertigo symptomology in more than 95% of cases, including the disappearance of vertigo attacks.

Acetyl-DL-leucine has been used in France to treat acute vertigo since 1957. A FDG-μPET study in a rat model of an acute unilateral labyrinthectomy (Zwergal et al. (2016) *Brain Struct Funct;* 221(1): 159-70) showed a significant effect of an L-enantiomer, N-acetyl-L-leucine, on postural compensation by activation of the vestibulo-cerebellum and a deactivation of the posterolateral thalamus (Gunther et al. (2015) *PLoS One;* 10(3): e0120891). The symptomatic improvement of cerebellar ataxia using acetyl-DL-leucine was shown in a case series with cerebellar patients (Strupp et al. (2013) *J Neurol;* 260(10): 2556-61). Another case series did not find benefit (Pelz et al. (2015) *J Neurol;* 262(5): 1373-5). Quantitative gait analysis showed that acetyl-DL-leucine improved temporal gait variability in patients with cerebellar ataxia (Schniepp et al. (2015) *Cerebellum;* 3:8). In a one-month study involving 12 patients with Niemann-Pick Type C (NPC), symptomatic improvement of ataxia was shown (Bremova et al. (2015) *Neurology;* 85(16): 1368-75). Further, a PET study in patients with ataxia given acetyl-DL-leucine demonstrated an increased metabolism in the midbrain and lower brainstem in responders (Becker-Bense et al. (2015) *Abstract EAN*).

Acetyl-leucine, however, is not known to treat RLS. As evidenced by the examples described herein, it has been found in accordance with the present disclosure that leucine, acetyl-leucine, or a pharmaceutically acceptable salt thereof can be used in a method of treating RLS, for example, by significantly reducing the severity of a patient's RLS.

In one embodiment, the present disclosure provides leucine, acetyl-leucine, or a pharmaceutically acceptable salt thereof, for use in a method of treating RLS or one or more symptoms associated with RLS in a subject in need thereof In one embodiment, the present disclosure includes leucine, acetyl-leucine, or a pharmaceutically acceptable salt thereof, for use in a method of treating RLS or one or more symptoms associated with RLS in a subject in need thereof, wherein the method comprises administering to the subject a therapeutically effective amount of the leucine, acetyl-leucine, or pharmaceutically acceptable salt thereof.

In one embodiment, leucine, acetyl-leucine or a pharmaceutically acceptable salt thereof is disclosed for use in a method for diminishing, inhibiting, or eliminating one or more symptoms associated with RLS in a subject in need thereof.

In one embodiment, the present disclosure includes leucine, acetyl-leucine or a pharmaceutically acceptable salt thereof for use in a method for diminishing, inhibiting, or eliminating one or more symptoms associated with RLS in a subject in need thereof, wherein the method comprises administering to the subject a therapeutically effective amount of the leucine, acetyl-leucine, or pharmaceutically acceptable salt thereof.

In another embodiment of the present disclosure, there is disclosed a method of diminishing, inhibiting, or eliminating one or more symptoms of restless legs syndrome (RLS) in a subject in need thereof, comprising administering a therapeutically effective amount of leucine, acetyl-leucine, or a pharmaceutically acceptable salt thereof to the subject.

A "subject," as used herein, may be a vertebrate, mammal or domestic animal. Hence, compositions according to the disclosure may be used to treat any mammal, for example livestock (e.g. a horse, cow, sheep or pig), pets (e.g. a cat, dog, rabbit or guinea pig), a laboratory animal (e.g. a mouse or rat), or may be used in other veterinary applications. In one embodiment, the subject is a human being. "Subject" and "patient" are used interchangeably.

As used herein, the singular forms "a," "an," and "the" include plural reference. The terms "approximately" and "about" mean to be nearly the same as a referenced number or value including an acceptable degree of error for the quantity measured given the nature or precision of the measurements.

As used herein, the terms "approximately" and "about" should be generally understood to encompass 35 20% of a specified amount, frequency or value. Numerical quantities given herein are approximate unless stated otherwise, meaning that term "about" or "approximately" can be inferred when not expressly stated.

The terms "administer," "administration," or "administering" as used herein refer to (1) providing, giving, dosing and/or prescribing by either a health practitioner or his authorized agent or under his direction a composition according to the disclosure, and (2) putting into, taking or consuming by the patient or person himself or herself, a composition according to the disclosure.

References to "leucine" and "acetyl-leucine" throughout include pharmaceutically acceptable salts of the same, even if not expressly stated.

The leucine or acetyl-leucine may be in racemic form, which means that the compound comprises about equal amounts of enantiomers. Alternatively it may be present in an enantiomeric excess of either the L-enantiomer or the D-enantiomer. The leucine or acetyl-leucine may be in a single enantiomeric form of either the L-enantiomer or the D-enantiomer. In one embodiment, the single enantiomeric form is the L-enantiomer. The racemic and enantiomeric forms may be obtained in accordance with known procedures in the art.

A "pharmaceutically acceptable salt" as referred to herein, is any salt preparation that is appropriate for use in a pharmaceutical application. Pharmaceutically acceptable salts include, but are not limited to, amine salts, such as N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chloro-benzyl-2-pyrrolidin-1'-ylmethylbenzimidazole, diethylamine and other alkylamines, piperazine, tris(hydroxymethyl)aminomethane and the like; alkali metal salts, such as lithium, potassium, sodium and the like; alkali earth metal salts, such as barium, calcium, magnesium and the like; transition metal salts, such as zinc, aluminum and the like; other metal salts, such as sodium hydrogen phosphate, disodium phosphate and the like; mineral acids, such as hydrochlorides, sulfates and the like; and salts of organic acids, such as acetates, lactates, malates, tartrates, citrates, ascorbates, succinates, butyrates, valerates, fumarates and the like.

The leucine, acetyl-leucine, or a pharmaceutically acceptable salt of the same, may be formulated and administered to a subject in accordance with known teachings in the art. For example, the leucine, acetyl-leucine, or a pharmaceutically acceptable salt thereof, may be formulated as a pharmaceutical composition. The pharmaceutical composition may comprise leucine, acetyl-leucine, or a pharmaceutically acceptable salt thereof, and a pharmaceutically acceptable carrier. Reference to the pharmaceutical composition encompasses the active agent alone (e.g., leucine, acetyl-leucine, or a pharmaceutically acceptable salt thereof) or in the form of a pharmaceutical composition.

The pharmaceutical composition may take any of a number of different forms depending, in particular, on the manner in which it is to be used. Thus, for example, it may be in the form of a powder, tablet, capsule, liquid, ointment, cream, gel, hydrogel, aerosol, spray, micellar solution, transdermal patch, liposome suspension or any other suitable form that may be administered to a person or animal in need of treatment.

A "pharmaceutically acceptable carrier" as referred to herein, is any known compound or combination of known compounds that are known to those skilled in the art to be useful in formulating pharmaceutical compositions. It will be appreciated that the carrier of the pharmaceutical composition should be one which is tolerated by the subject to whom it is given.

In one embodiment, the pharmaceutically acceptable carrier may be a solid, and the composition may be in the form of a powder or tablet. A solid pharmaceutically acceptable carrier may include, but is not limited to, one or more substances which may also act as flavouring agents, buffers, lubricants, stabilisers, solubilisers, suspending agents, wetting agents, emulsifiers, dyes, fillers, glidants, compression aids, inert binders, sweeteners, preservatives, dyes, coatings, or tablet-disintegrating agents. The carrier may also be an encapsulating material. In powders, the carrier may be a finely divided solid that is in admixture with the finely divided active agents according to the invention. In tablets, the active agent may be mixed with a carrier having the necessary compression properties in suitable proportions and compacted in the shape and size desired. The powders and tablets may, for example, contain up to 99% of the active agents. Suitable solid carriers include, for example, calcium phosphate, magnesium stearate, talc, sugars, lactose, dextrin, starch, gelatin, cellulose, polyvinylpyrrolidine, low melting waxes and ion exchange resins. In another embodiment, the pharmaceutically acceptable carrier may be a gel and the composition may be in the form of a cream or the like.

The carrier may include, but is not limited to, one or more excipients or diluents. Examples of such excipients are gelatin, gum arabicum, lactose, microcrystalline cellulose, starch, sodium starch glycolate, calcium hydrogen phosphate, magnesium stearate, talcum, colloidal silicon dioxide, and the like.

In another embodiment, the pharmaceutically acceptable carrier may be a liquid. In one embodiment, the pharmaceutical composition is in the form of a solution. Liquid carriers are used in preparing solutions, suspensions, emulsions, syrups, elixirs and pressurized compositions. The leucine, acetyl-leucine, or pharmaceutically acceptable salt thereof may be dissolved or suspended in a pharmaceutically acceptable liquid carrier such as water, an organic solvent, a mixture of both or pharmaceutically acceptable oils or fats. The liquid carrier may contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid carriers for oral and parenteral administration include water (partially containing additives as above, e.g. cellulose derivatives, such as sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier may also be an oily ester such as ethyl oleate and isopropyl myristate. Sterile liquid carriers are useful in sterile liquid form compositions for parenteral administration. The liquid carrier for pressurised compositions may be a halogenated hydrocarbon or other pharmaceutically acceptable propellant.

Liquid pharmaceutical compositions, which are sterile solutions or suspensions, may be utilised by, for example, intramuscular, intrathecal, epidural, intraperitoneal, intravenous and subcutaneous injection. The active agent may be prepared as a sterile solid composition that may be dissolved or suspended at the time of administration using sterile water, saline, or other appropriate sterile injectable medium.

The compositions may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The compositions may also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Compositions may alternatively be administered by inhalation (e.g. intranasally). Compositions may also be formulated for topical use. For instance, creams or ointments may be applied to the skin.

Leucine, acetyl-leucine, or a pharmaceutically acceptable salt thereof may be incorporated within a slow- or delayed-release device. Such devices may, for example, be inserted on or under the skin, and the medicament may be released over weeks or even months. Such devices may be advantageous when long-term treatment with leucine or acetyl-leucine used according to the present disclosure is required and which may require frequent administration (e.g. at least daily administration).

In one embodiment, the pharmaceutical composition is a solid oral dosage form, such as a tablet. In tablets, the active agent may be mixed with a vehicle, such as a pharmaceutically acceptable carrier, having the necessary compression properties in suitable proportions and compacted in the shape and size desired. The tablets may contain up to 99% by weight of the active agents.

Pharmaceutical compositions in solid oral dosage form, such as tablets, may be prepared by any method known in the art of pharmacy. Pharmaceutical compositions are usually prepared by mixing the active agent with conventional pharmaceutically acceptable carriers.

A tablet may be formulated as is known in the art. Tanganil®, for example, includes wheat starch, pregelatinised maize (corn) starch, calcium carbonate and magnesium stearate as excipients. The same, or similar, excipients, for example, may be employed with the present disclosure.

The composition of each 700 mg Tanganil® tablet is as follows: 500 mg acetyl-DL-leucine, 88 mg wheat starch, 88 mg pregelatinised maize (corn) starch, 13 mg calcium carbonate and 11 mg magnesium stearate. The same tablets, for example, may be employed with the present disclosure.

As discussed above, the leucine, acetyl-leucine, or pharmaceutically acceptable salt thereof may be formulated and administered as a pharmaceutical composition taking any number of different forms. For example, the leucine, acetyl-leucine or pharmaceutically acceptable salt thereof may be formulated as a pharmaceutical composition to facilitate its delivery across the blood-brain barrier. As a further example, the leucine, acetyl-leucine or pharmaceutically acceptable salt thereof may be formulated as a pharmaceutical composition for bypassing the blood-brain barrier. Formulations that facilitate delivery across the blood-brain barrier or that are suitable for administration in a manner that bypasses the blood-brain barrier may be used to prepare and administer leucine (not acetylated) as described herein.

In one embodiment, the pharmaceutical composition (e.g., comprising leucine or salt thereof) is formulated for nanodelivery, e.g., colloidal drug-carrier systems. Suitable examples include but are not limited to liposomes, nanoparticles (e.g., polymeric, lipid and inorganic nanoparticles), nanogels, dendrimers, micelles, nanoemulsions, polymersomes, exosomes, and quantum dots. See, e.g., Patel et al., "Crossing the Blood-Brain Barrier: Recent Advances in Drug Delivery to the Brain," CNS Drugs 31:109-133 (2017); Kabanov et al., "New Technologies for Drug Delivery across the Blood Brain Barrier," Curr Pharm Des., 10(12):1355-1363 (2004); Cheng et al., "Highly Stabilized Curcumin Nanoparticles Tested in an In Vitro Blood—Brain Barrier Model and in Alzheimer's Disease Tg2576 Mice," The AAPS Journal, vol. 15, no. 2, pp. 324-336 (2013); Lähde et al. "Production of L-Leucine Nanoparticles under Various Conditions Using an Aerosol Flow Reactor Method," Journal of Nanomaterials, vol. 2008, article ID 680897 (2008).

In one embodiment, the pharmaceutical composition (e.g., comprising leucine or a salt thereof) is formulated for direct delivery to the central nervous system (CNS), such as by injection or infusion. Formulations for and methods of direct delivery to the CNS are known in the art. See, e.g., U.S. Pat. No. 9,283,181. Examples of such administration include but are not limited to intranasal, intraventricular, intrathecal, intracranial, and delivery via nasal mucosal grafting.

In one embodiment, the pharmaceutical composition is formulated for (and administered by) intranasal delivery. See, e.g., Hanson et al., "Intranasal delivery bypasses the blood-brain barrier to target therapeutic agents to the central nervous system and treat neurodegenerative disease," BMC Neurosci. 9(Suppl 3):S5 (2008). In one embodiment, the pharmaceutical composition is formulated for (and administered by) delivery via a nasal mucosal graft. In one embodiment, the pharmaceutical composition is formulated for (and administered by) intracerebroventricular injection or infusion. In another embodiment, the pharmaceutical composition is formulated for (and administered by) intrathecal intracisternal injection or infusion. In one embodiment, the pharmaceutical composition is formulated for (and administered by) intrathecal lumbar injection or infusion.

Various techniques may be used including, without limitation, injection through a burrhole or cisternal or lumbar puncture or the like as known in the art. Various devices, whether internal (e.g., implanted) or external, may be used for delivery as known in the art, such as pumps, catheters, reservoirs, etc. In one embodiment, the administration interval is once every two weeks.

In one embodiment, the administration interval is once every month. In one embodiment, the administration interval is once every two months. In one embodiment, the administration interval is twice per month. In one embodiment, the administration interval is once every week. In one embodiment, the administration interval is twice or several times per week. In one embodiment, the administration interval is daily. In one embodiment, the administration is continuous, such as continuous infusion.

In one embodiment, leucine, or a pharmaceutically acceptable salt thereof, may be administered in a dose or amount equivalent to those disclosed herein for acetyl-leucine, adjusted to account for either its direct delivery to the CNS or its delivery across the blood-brain barrier.

Similarly, acetyl-leucine, or a pharmaceutically acceptable salt thereof may be administered in a dose or amount as disclosed herein; the dose may be adjusted according to its route of administration (e.g., direct delivery to the CNS).

The present disclosure describes leucine, acetyl-leucine, and pharmaceutically acceptable salts thereof, including compositions and methods thereof, for treating RLS or one or more symptoms associated with RLS in a subject in need thereof.

A "subject in need thereof" as used herein may be any subject who has RLS or one or more symptoms associated with RLS, and may also include any subject or patient who is at risk or believed to be at risk of developing RLS or one or more symptoms associated with RLS. The subject may or may not have been diagnosed with RLS. For example, the subject may not yet have a diagnosis (clinical or otherwise) of RLS but may have one or more symptoms of RLS. The subject may have a genetic, biochemical, or other similar identifiable marker of RLS or of an underlying condition to which RLS may be associated. The subject in need thereof may be suspected of having or at risk of having RLS. For example, the subject may have a genetic predisposition to RLS (e.g., the subject may have one or more family members with RLS).

A "therapeutically effective amount" of an agent is any amount which, when administered to a subject, is the amount of agent that is needed to produce the desired effect, which, for the present disclosure, can be therapeutic and/or prophylatic. The dose may be determined according to various parameters, such as the specific form of leucine or acetyl-leucine used; the age, weight and condition of the patient to be treated; the route of administration; and the required regimen. A physician will be able to determine the required route of administration and dosage for any particular patient. For example, a daily dose may be from about 10 to about 225 mg per kg, from about 10 to about 150 mg per kg, or from about 10 to about 100 mg per kg of body weight.

As used herein, "treating" or "treatment" refers to any indicia of success in the prevention or amelioration of an injury, pathology or condition of RLS and/or prevention or amelioration of one or more symptoms associated with RLS, including any objective or subjective parameter such as abatement; remission; diminishing, inhibiting, or elimination of symptoms or making the injury, pathology, or condition more tolerable to the subject; slowing in the rate of degeneration or decline or worsening of the disorder; or improving the physical or mental well-being of the subject in need thereof. Treatment for RLS or one or more symptoms associated with RLS can be based on objective and/or subjective parameters, including, e.g., the results of physical examination(s), neurological examination(s), and/or psychiatric evaluation(s).

"Restless legs syndrome" (i.e., "RLS") as used herein includes any form of RLS, including primary RLS and secondary RLS. In one embodiment, the RLS is primary RLS. In another embodiment, the RLS is secondary RLS. In one embodiment, the RLS is secondary to a disease or medical condition. Examples of such diseases or medical conditions include iron deficiency, renal failure, uremia, peripheral neuropathy, varicose veins, a neurodegenerative disease, stress, sleep deprivation, fibromyalgia, hyper- or hypothyroidism, pregnancy, cigarette smoking, vitamin deficiency (e.g., vitamin B-12 deficiency), mineral deficiency (e.g., magnesium deficiency), amyloidosis, lyme disease, spinal nerve damage, rheumatoid arthritis, and Sjögren syndrome. In one embodiment, the RLS is secondary to a medication or substance. Examples of such medications or substances include alcohol, caffeine, anticonvulsant drugs (e.g., phenytoin), antidepressants (e.g., amitriptyline, paroxetine), medication for high blood pressure (e.g., beta-blockers), antipsychotics, and withdrawal from medication(s) (e.g., vasodilator drugs, sedatives, antidepressants). Examples of neurodegenerative diseases include Parkinson's Disease, Huntington's disease, hereditary spastic paraparesis, amyotrophic lateral sclerosis (ALS), Alzheimer's disease, frontotemporal dementia, dementia with Lewy bodies, multiple system atrophy, progressive supranuclear palsy, and corticobasal degeneration. In one embodiment, the neurodegenerative disease is a Motor Neuron Disease (e.g., progressive bulbar palsy (PBP), pseudobulbar palsy, primary lateral sclerosis (PLS), amyotrophic lateral sclerosis (ALS), progressive muscular atrophy (PMA), Huntington's disease, multiple sclerosis, Parkinson's Disease, Canavan disease, frontotemporal lobar degeneration, narcolepsy, Pelizaeus-Merzbacher disease, and spinal muscular atrophy). In one embodiment, the neurodegenerative disease is parkinsonism, including primary or idiopathic, secondary or acquired, hereditary parkinsonism, and Parkinson plus syndromes or multiple system degeneration. In one embodiment, the disease or medical condition is associated with dopaminergic system dysfunction, such as dopaminergic cell loss.

A "symptom" associated with RLS includes any clinical or laboratory manifestation associated with RLS. Symptoms of RLS are often, but need not be, manifestations associated with the disease that the subject can feel or observe. Symptoms associated with RLS include, but are not limited to, lower leg sensations, periodic limb movements of sleep (PLMS), unpleasant leg sensation, urge to move, restlessness, sleep disturbances, excessive daytime sleepiness and the like.

In one embodiment, leucine, acetyl-leucine or a pharmaceutically acceptable salt thereof is used in a method for diminishing, inhibiting, or eliminating one or more symptoms associated with RLS in a subject in need thereof. The method comprises administering to the subject a therapeutically effective amount of the leucine, acetyl-leucine, or pharmaceutically acceptable salt thereof. In one embodiment, the one or more symptoms are chosen from any one or combination of lower leg sensations, periodic leg movements of sleep, unpleasant leg sensations, urge to move, restlessness, excessive daytime sleepiness, and sleep disturbances.

The severity of RLS or one or more symptoms of RLS may be assessed, e.g., using a known scale, index, rating, or score. For example, the scale, index, rating, score, or other suitable test may correspond to the severity of the RLS overall or to the severity of one or more symptoms associated with RLS. In one embodiment, the treatment described herein improves such an assessment from a value or degree characteristic of a symptomatic subject to a value or degree characteristic of a non-symptomatic subject. In one embodiment, the treatment described herein improves such an assessment compared to a baseline. The baseline may be, for example, the subject's condition before initiating any treatment for RLS or before initiating treatment for RLS with leucine, acetyl-leucine, or a pharmaceutically acceptable salt thereof. Alternatively, the baseline may be, for example, the subject's condition after a certain time period on treatment for RLS.

In one embodiment, treatment with leucine, acetyl-leucine, or a pharmaceutically acceptable salt thereof as described herein decreases the subject's International Restless Leg Syndrome Study Group Rating Scale ("IRLS") compared to a baseline. In one embodiment, the IRLS is reduced compared to baseline by at least 10%, at least 20%, at least 30%, at least 40%, or at least 50%. In one embodiment, the IRLS is reduced by at least 60%, at least 70%, at least 80%, at least 90%, or 100%.

In one embodiment, acetyl-leucine, or a pharmaceutically acceptable salt of the same, may be administered, for example, at a dose ranging from about 500 mg to about 15 g per day or ranging from about 500 mg to about 10 g per day, such as ranging from about 1.5 g to about 10 g per day, optionally by solid oral or liquid oral route. The acetyl-leucine, or a pharmaceutically acceptable salt of the same, may be administered, for example, in a dose according to that of Tanganil®, which is prescribed to adults in a dose of 1.5 g to 2 g per day, 3-4 tablets in two doses, morning and evening.

If one enantiomer is administered, the doses may be reduced accordingly. For instance if only acetyl-L-leucine or if only acetyl-D-leucine is administered, the dose may range from about 250 mg to about 15 g per day, range from about 250 mg to about 10 g per day, or range from about 250 mg to about 5 g per day, such as from about 0.75 g to about 5 g per day.

In one embodiment, the administered dose ranges from about 1 g to about 15 g per day, from about 1 g to about 10 g per day, or from about 1.5 g to about 7 g per day. It may be from about 2, 3, 4, 5, 6, 7, 8, 9, 10, 11, 12, 13, or 14 g to about 15 g per day. It may be from about 2, 3, 4, 5, 6, 7, 8 or 9 g to about 10 g per day. It may be more than about 1.5 g per day, but less than about 15, 14, 13, 12, 11, 10, 9, 8, 7, 6 or 5 g per day. In one embodiment, the dose ranges from about 4 g to about 6 g per day. In one embodiment, the dose ranges from about 4 g to about 5 g per day. In one embodiment, the dose is about 4.5 g per day. In one embodiment, the dose is about 5 g per day. In one embodiment, these doses are administered in a solid oral dosage form, notably tablets. In another embodiment, these doses are for acetyl-leucine when in its racemic form. Doses for acetyl-leucine when an enantiomeric excess is present may be lower than those recited here, for example, around 50% lower. The above recited dose-ranges when halved are thus also explicitly encompassed by the present disclosure.

In one embodiment, the total daily dose may be spread across multiple administrations, i.e. administration may occur two or more times a day to achieve the total daily dose. As an example, the required number of tablets to provide the total daily dose of acetyl-leucine may be split across two administrations (for example, in the morning and evening) or three administrations (for example, in the morning, noon and evening). Each dose may be suitably administered with or without food. For example, acetyl-leucine may be dosed by about 1 or about 2 hours before meals, such as at least about 20 minutes, at least about 30 minutes, at least about 40 minutes, or at least about 1 hour before meals, or may be dosed by about 1, about 2, or about 3 hours after meals, such as waiting at least about 20 minutes, at least about 30 minutes, at least about 1 hour, at least about 1.5 hours, at least about 2 hours, or at least about 2.5 hours after meals. For example, a total daily dose of 4.5 g acetyl-DL-leucine may be administered as three Tanganil® (or equivalent) tablets before, with, or after breakfast, three further tablets before, with, or after lunch and three further tablets before, with, or after dinner.

Administration of leucine or acetyl-leucine in accordance with the present disclosure may be initiated before or after a subject is found to have a genetic, biochemical, or other similar identifiable marker of RLS or a medical condition or disease to which RLS is associated. Administration may be initiated at or around the time a subject is found to have a genetic, biochemical, or other similar identifiable marker of RLS. Similarly, administration may be initiated at or around the time a subject is diagnosed with RLS.

Treatment duration may be, for example, about seven days or more, about two weeks or more, about three weeks or more, about one month or more, about six weeks or more, about seven weeks or more, or about two months or more. In one embodiment, it is about three months or more, about four months or more, about five months or more or about six months or more. The treatment duration may be about 1 year or more, about 2 years or more, about 4 years or more, about 5 years or more, or about 10 years or more. The treatment duration may be the life-time of the patient.

Any and all combinations of dosage form, dose amount, dosing schedule and treatment duration are envisaged and encompassed by the disclosure. In one embodiment, the dose is from about 4 g to about 10 g per day, taken across one, two, or three administrations per day, for a treatment duration of about two months or more. In another embodiment, the dose is more than 4 g but no more than 5 g per day, taken across one, two, or three administrations per day, for a treatment duration of about six months or more. The dosage form may be a solid oral dosage form, notably tablets.

The pharmaceutical compositions described herein may be used as a monotherapy (e.g., use of the active agent alone) for treating RLS in a subject. Alternatively, the pharmaceutical compositions may be used as an adjunct to, or in combination with, other known therapies, e.g., for treating RLS and/or for treating an underlying medical condition or disease.

There is also provided a method of treating RLS or one or more symptoms associated with RLS in a subject in need thereof, the method comprising administering a therapeutically effective amount of leucine, acetyl-leucine, or a pharmaceutically acceptable salt thereof to the subject.

In one embodiment, administering a therapeutically effective amount of leucine, acetyl-leucine, or a pharmaceutically acceptable salt thereof to the subject in need thereof diminishes, inhibits, or eliminates one or more symptoms associated with RLS. In one embodiment, the one or more symptoms are chosen from any one or combination of lower leg sensations, periodic leg movements of sleep, unpleasant leg sensations, urge to move, restlessness, excessive daytime sleepiness, and sleep disturbances.

Also disclosed is a kit for treating RLS in a subject, comprising a means for diagnosing or prognosing RLS, and leucine, acetyl-leucine or a pharmaceutically acceptable salt thereof.

The kit may further comprise buffers or aqueous solutions. The kit may further comprise instructions for using the leucine, acetyl-leucine or pharmaceutically acceptable salt thereof according to a method of the present disclosure.

All of the features described herein (including any accompanying claims, abstract and drawings), and/or all of the steps of any method so disclosed, may be combined with any of the above aspects in any combination, except combinations where at least some of such features and/or steps are mutually exclusive.

EXAMPLES

Patient 1

The patient in this case study was a 55-year-old female showing proximal weakness of the lower limb. She had a flexor paresis of the head slowly progressive since age 42 and had been diagnosed (genetically confirmed) with myotonic dystrophy type 2. Upon consultation at age 55, she reported no sensory symptoms but complained of a restless leg syndrome at night and during resting periods of the day, occurring over the course of the last two years. Pre-treatment with dopamine agonist were without symptom relief.

Serum creatine kinase activity was only mildly elevated at up to 400 IU/L. The patient was evaluated using the RLS diagnostic index (RLS-DI) (see Walters et al., Sleep Med 2003; 4(2):121-132;). The patient's International Restless Legs Syndrome Rating Scale score (IRLS) was 36, and thus a severe RLS was diagnosed. The patient was started on therapy with acetyl-DL-leucine at a dose of 3 g per day for the first week, followed by a dose of 5 g per day for the second week onwards. Within 14 days on acetyl-DL-leucine, the IRLS dropped to 26, and after another 5 weeks, the IRLS declined to 9. Interruption of 4 weeks of the treatment after week 12 of the treatment increased the IRLS to 28. Re-introduction of the treatment re-declined the score to 8 after 2 weeks. Continuation of treatment over more than 22 weeks stabilized the IRLS score at 8.

Patient 2

The patient in this case study was a 72-year-old female showing proximal weakness of the lower limb. She had a flexor paresis of the head slowly progressive since age 48 and had been diagnosed (genetically confirmed) with myotonic dystrophy type 2 15 years ago. Upon consultation at age 72, she reported no sensory symptoms but complained of a restless leg syndrome at night and during resting periods of the day, occurring over the course of the last eight years. Pre-treatment with dopamine agonist, L-dopa, pregabaline, and opiods were without sustained symptom relief. Serum creatine kinase activity was mildly elevated at 300 IU/L. Iron measurements and all additional lab investigations were normal. The patient was evaluated using the RLS-DI and the patient's IRLS was 32, and thus a moderate to severe RLS was diagnosed. The patient was started on therapy with acetyl-DL-leucine at a dose of 3 g per day for the first week, followed by a dose of 5 g per day for the second week onwards. Within 14 days on acetyl-DL-leucine, the IRLS dropped to 22, and after another 5 weeks, the IRLS declined to 7. Continuation of treatment over more than 28 weeks stabilized the IRLS score at 8.

Patient 3

The patient in this case study was a 73-year-old male showing mild proximal weakness of the upper and lower limbs slowly progressive since age 50. The patient had been diagnosed (genetically confirmed) with McArdle myopathy about 16 years ago. Upon consultation at age 73, he reported no sensory symptoms but complained about a severe fatigue and reduced stamina. The patient further reported a restless leg syndrome at night and during resting periods of the day, occurring over the course of the last 12 years. Pre-treatment with dopamine agonist, L-dopa, pregabaline were without sustained symptom relief. Serum creatine kinase activity was mildly elevated at 200 IU/L; however, the patient had 5 episodes of rhabdomyolysis during the past 20 years. Repeated iron measurements and all additional lab investigations were normal. The patient was evaluated using the RLS-DI and the patient's IRLS was 34, and thus a severe RLS was diagnosed. The patient was started on therapy with acetyl-DL-leucine at a dose of 3 g per day for the first week, followed by a dose of 5 g per day for the second week onwards. Within 21 days on acetyl-DL-leucine, the IRLS dropped to 20, and after another 10 weeks, the IRLS declined to 10. Continuation of treatment over more than 30 weeks stabilized the IRLS score at 10. In addition, the patient's fatigue declined (Fatigue Severit Scale: 9 (minimum) to 63 (maximum)) from 53 to 28.

Patient 4

The patient in this case study was a 59-year-old female showing symptoms of RLS and with RLS of unknown etiology. Upon consultation at age 59, she reported no sensory symptoms but complained of a restless leg syndrome at night and during resting periods of the day, occurring over the course of the at least 15 years. Pre-treatment with dopamine agonist, L-dopa, pregabaline were without sustained relief. Iron measurements and all additional lab investigations were normal. The patient was evaluated using the RLS-DI and the patient's IRLS was 32, and thus a moderate to severe RLS was diagnosed. The patient was started on therapy with acetyl-DL-leucine at a dose of 3 g per day for the first week, followed by a dose of 5 g per day for the second week onwards. Within 14 days on acetyl-DL-leucine, the IRLS dropped to 8, and after another 2 weeks, the IRLS declined to 6. Continuation of treatment over more than 4 weeks stabilized the IRLS score at 6.

The invention claimed is:

1. A method of treating restless legs syndrome (RLS) or one or more symptoms associated with RLS in a subject in need thereof comprising:
   administering leucine, acetyl-leucine, or a pharmaceutically acceptable salt thereof to the subject.

2. The method according to claim 1, wherein the RLS is primary RLS.

3. The method according to claim 1, wherein the RLS is secondary RLS.

4. The method according to claim 1, wherein the method comprises administering to the subject a therapeutically effective amount of the leucine, acetyl-leucine, or pharmaceutically acceptable salt thereof.

5. The method according to claim 4, wherein the administration occurs over time and the subject's International Restless Leg Syndrome Rating Scale (IRLS) is reduced by at least 10% after the administration compared to a baseline.

6. The method according to claim 5, wherein the subject's IRLS is reduced by at least 50% after the administration compared to a baseline.

7. The method according to claim 1, wherein the leucine is DL-leucine.

8. The method according to claim 1, wherein the acetyl-leucine is acetyl-DL-leucine.

9. The method according to claim 1, wherein the leucine has an enantiomeric excess of the L-enantiomer or the D-enantiomer.

10. The method according to claim 1, wherein the acetyl-leucine has an enantiomeric excess of the L-enantiomer or the D-enantiomer.

11. The method according to claim 1, wherein the method comprises administering the acetyl-leucine to the subject in need thereof at a therapeutically effective amount chosen from about 1 g to about 15 g per day, about 1 g to about 10 g per day, about 1.5 g to about 7 g per day, about 4 g to about 6 g per day, and about 4 g to about 5 g per day.

12. A method of diminishing, inhibiting, or eliminating one or more symptoms of restless legs syndrome (RLS) in a subject in need thereof comprising:
   administering a therapeutically effective amount of leucine, acetyl-leucine, or a pharmaceutically acceptable salt thereof to the subject.

13. The method according to claim 12, wherein the one or more symptoms are chosen from lower leg sensations, periodic leg movements of sleep, unpleasant leg sensations, urge to move, restlessness, daytime sleepiness, and sleep disturbances.

14. The method according to claim 12, wherein the leucine is DL-leucine.

15. The method according to claim 12, wherein the acetyl-leucine is acetyl-DL-leucine.

16. The method according to claim 12, wherein the leucine has an enantiomeric excess of the L-enantiomer or the D-enantiomer.

17. The method according to claim 12, wherein the acetyl-leucine has an enantiomeric excess of the L-enantiomer or the D-enantiomer.

18. The method according to claim 12, wherein the therapeutically effective amount of the leucine, acetyl-leucine, or pharmaceutically acceptable salt thereof, is chosen from about 1 g to about 15 g per day, about 1 g to about 10 g per day, about 1.5 g to about 7 g per day, about 4 g to about 6 g per day, and about 4 g to about 5 g per day.

* * * * *